(12) United States Patent
Beneduce

(10) Patent No.: US 10,330,521 B2
(45) Date of Patent: Jun. 25, 2019

(54) UNIVERSAL WEIGHING AND BODILY INFORMATION DEVICE FOR FOOD RELATED AREAS

(71) Applicant: Vincent Beneduce, Vero Beach, FL (US)

(72) Inventor: Vincent Beneduce, Vero Beach, FL (US)

( * ) Notice: Subject to any disclaimer, the term of this patent is extended or adjusted under 35 U.S.C. 154(b) by 0 days.

(21) Appl. No.: 15/291,942

(22) Filed: Oct. 12, 2016

(65) Prior Publication Data

US 2017/0110029 A1 Apr. 20, 2017

Related U.S. Application Data

(60) Provisional application No. 62/241,822, filed on Oct. 15, 2015.

(51) Int. Cl.
*G01G 19/414* (2006.01)
*A61B 5/053* (2006.01)
*G01G 19/44* (2006.01)

(52) U.S. Cl.
CPC ....... *G01G 19/4146* (2013.01); *A61B 5/0537* (2013.01); *G01G 19/44* (2013.01)

(58) Field of Classification Search
CPC ............... G06Q 30/0201; G09B 19/00; G01G 19/4146; G01G 19/44; A61B 5/0537
See application file for complete search history.

(56) References Cited

U.S. PATENT DOCUMENTS

| | | | | |
|---|---|---|---|---|
| 6,649,848 | B2 * | 11/2003 | Kriger | G01G 19/4146 128/921 |
| 7,123,956 | B2 * | 10/2006 | Oguma | A61B 5/0537 600/547 |
| 2007/0233523 | A1 * | 10/2007 | Izumi | A61B 5/0537 705/3 |
| 2010/0258356 | A1 * | 10/2010 | Anandampillai | G01G 19/4146 177/25.16 |
| 2014/0251005 | A1 * | 9/2014 | Curry | G01F 23/0007 73/290 R |
| 2015/0107910 | A1 * | 4/2015 | Villard | G01G 19/4146 177/25.12 |

* cited by examiner

*Primary Examiner* — Michael C Zarroli
(74) *Attorney, Agent, or Firm* — Ingenium Patents LLC; Peter Kramer

(57) ABSTRACT

This device is a universal weighing and bodily information device that calculates the weight and bodily information of a subject(s) in food preparation, storage and consumption areas. The device is made to be used with any food related areas but not limited to those areas. The device can vary in size and shape, flat to flexible, varying in depth and height depending on application, with a display capable of placement inside refrigerator, cabinet, pantry or any other desired area. The base can be placed in desired areas with or without the use of filler panels. The base can be covered, at the user's option, with various materials that allow functionality. The information can be transmitted to a display, another device, or memory; any, either, or all, depending on user preference.

9 Claims, 8 Drawing Sheets

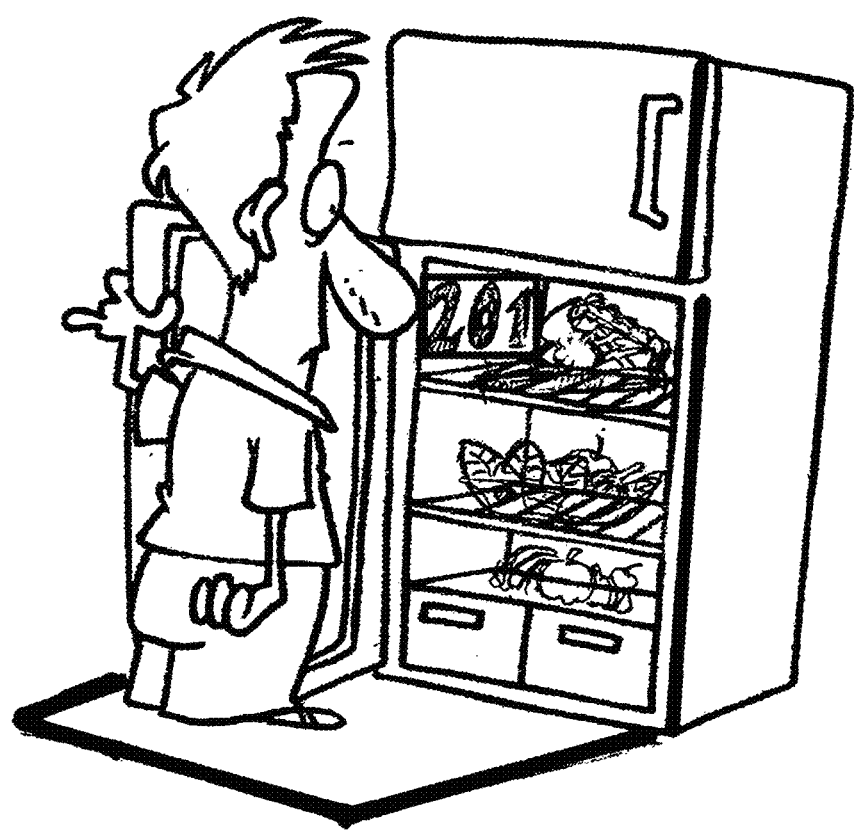
Fig. 1. Used with refrigerator

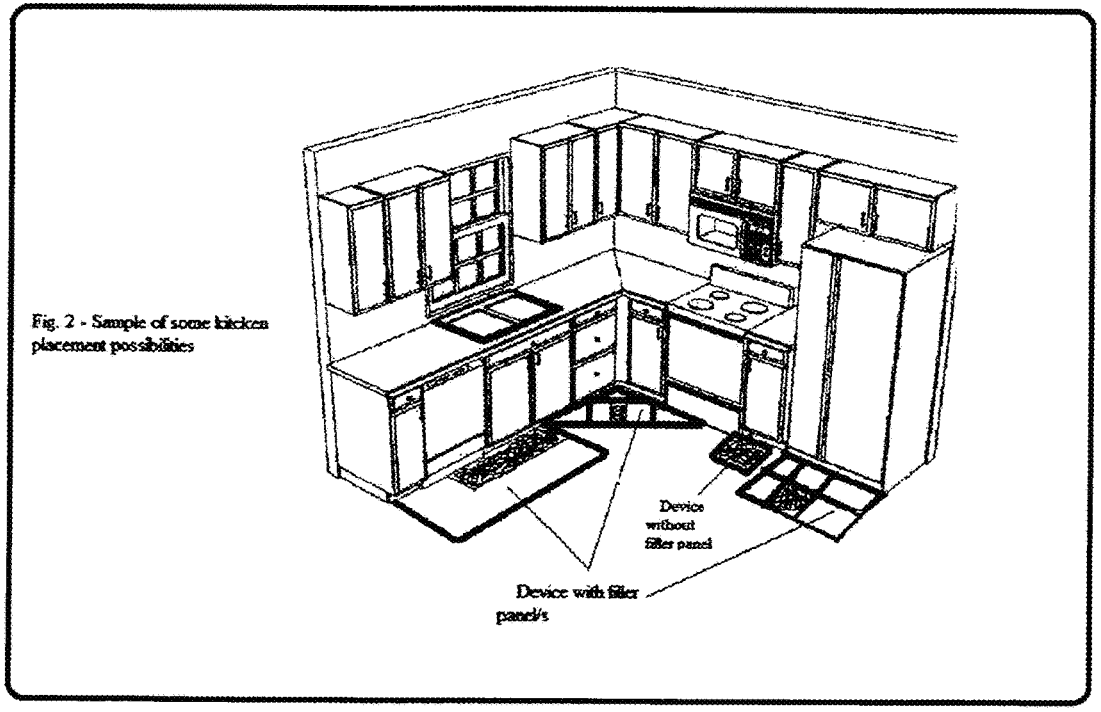
Fig. 2 - Sample of some kitchen placement possibilities
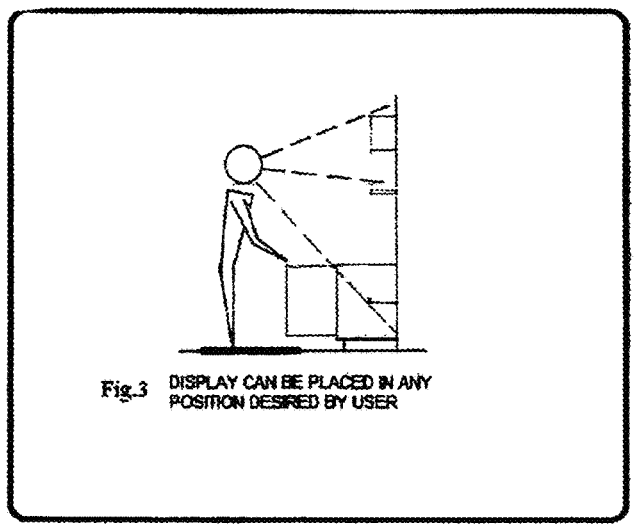
Fig. 3  DISPLAY CAN BE PLACED IN ANY POSITION DESIRED BY USER

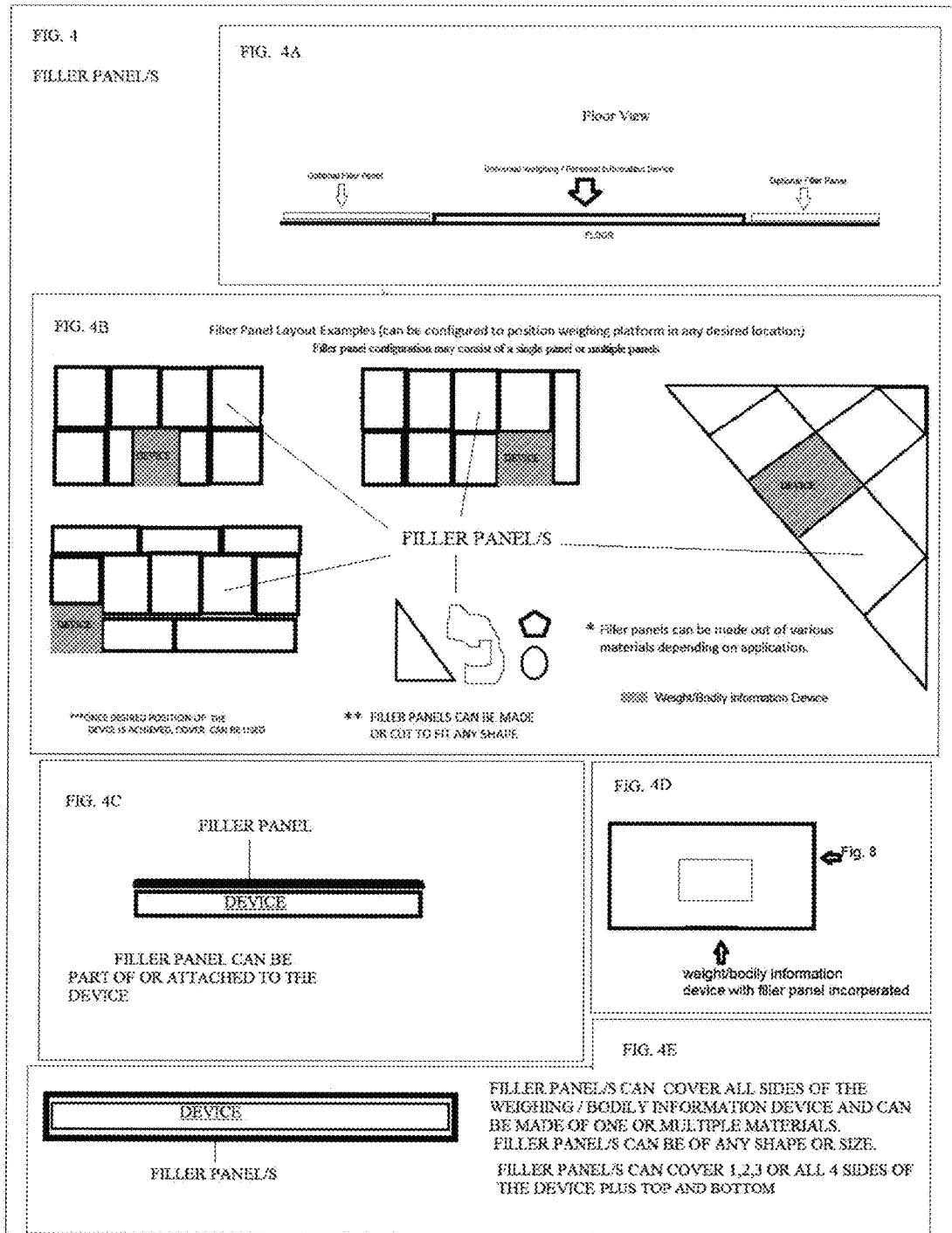

Fig. 5 Communication with device
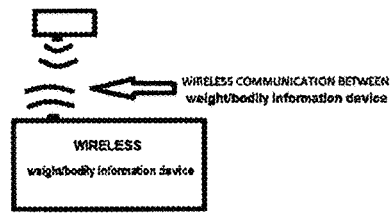
and / OR
COMMUNICATION BETWEEN DEVICES CAN BE EITHER METHOD OR A COMBINATION OF BOTH
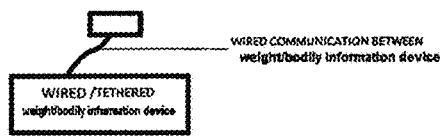
Fig. 6 Communication with display and / or another device
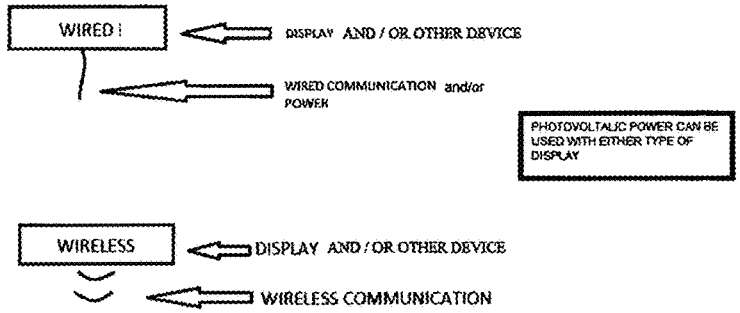

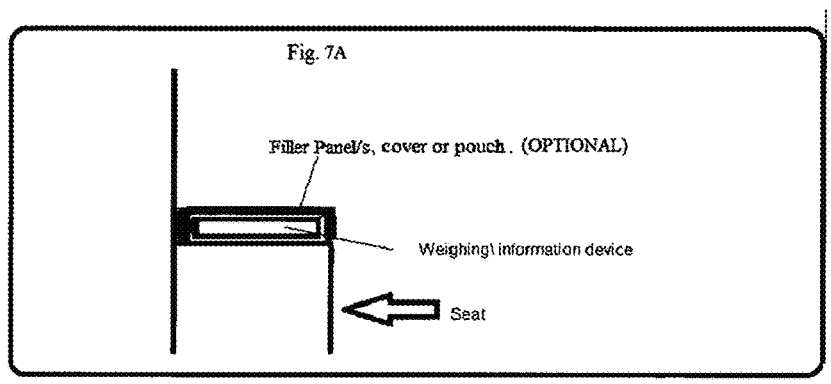
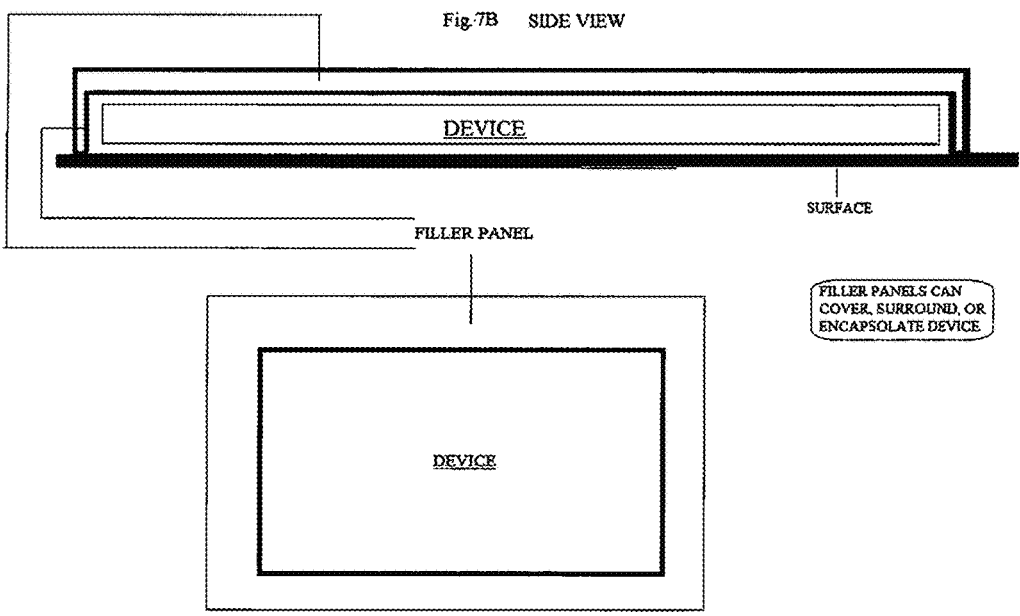

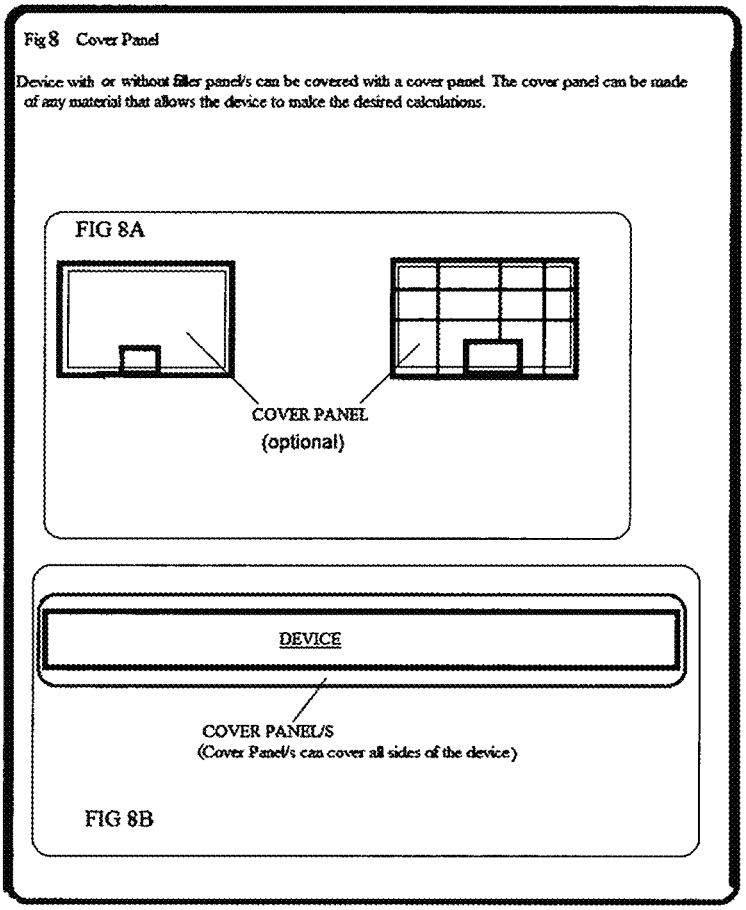

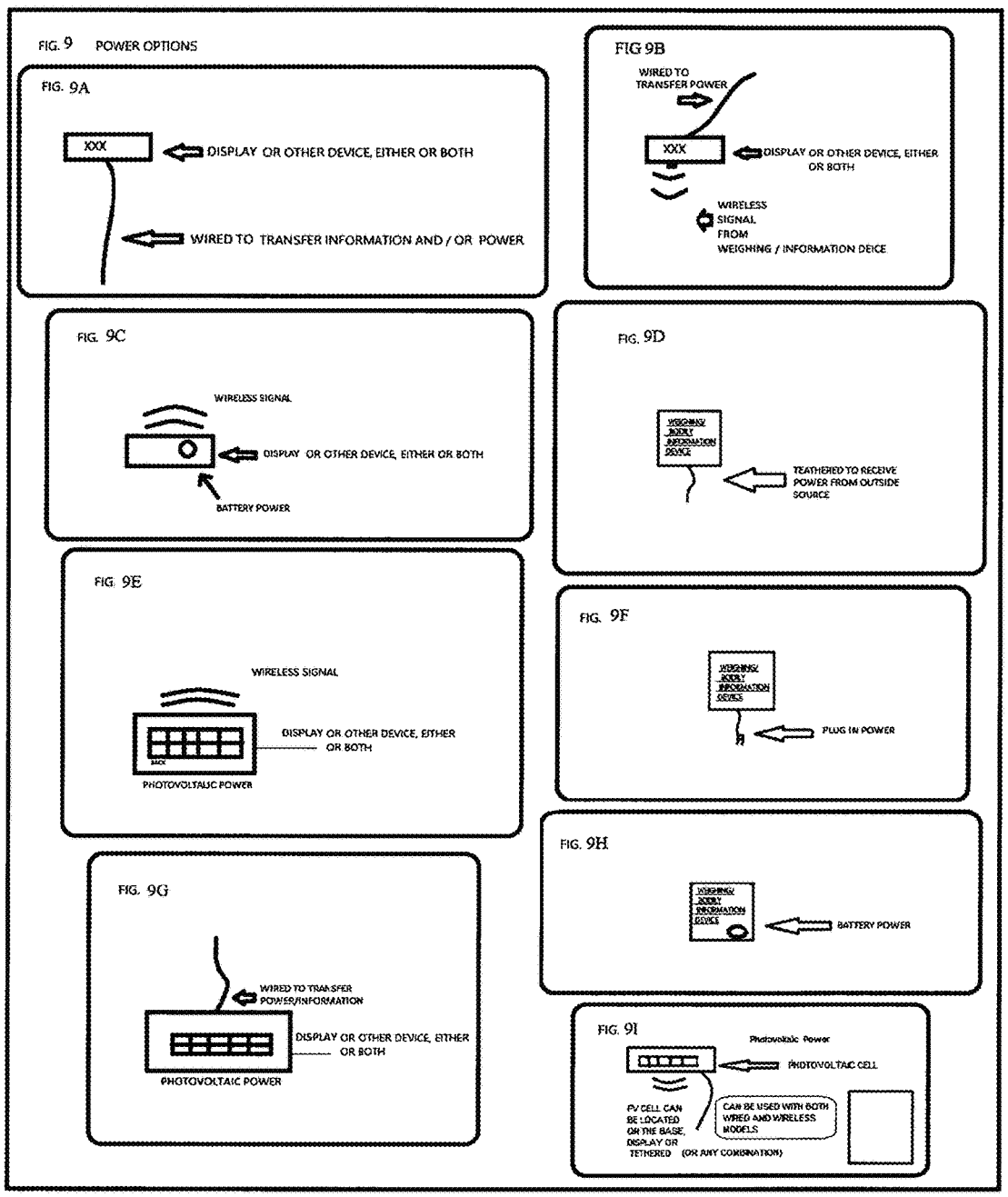

Fig. 10
Switches
← A manual switch can be installed on a door to activate device and/or display (either or both)
← A photo switch can be used to activate device and/or display (either or both)
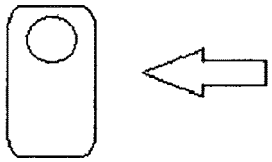
← A motion detecting switch can be used to activate device and/or display (either or both)
Device can also be set in constant on position

UNIVERSAL WEIGHING AND BODILY INFORMATION DEVICE FOR FOOD RELATED AREAS

The proposed invention is a universal weighing and bodily information device that calculates the weight and bodily information of a subject(s) in food preparation, storage and consumption areas. The information can be transmitted to a display, another device, or memory; any, either, or all, depending on user preference. The device can vary in size and shape, flat to flexible, varying in depth and height depending on application. This device is made to be used with any food related areas, weather that be in storage areas to encourage positive choices on the type of food to consume, or any other information, or consumption areas to monitor the amount of intake, or any other information, or food preparation areas to monitor portions, or any other information, or any other desired area. The base and display can be used with refrigerators, cabinets, food preparation areas, dining areas, seating areas, pantries or any other desired area. The base can be placed in desired areas with or without the use of filler panels. The base can be covered, at the user's option, with various materials that allow functionality. The base can be placed in any desired area and the subject will stand or sit on the device producing the weight and/or body information desired. The said information can either be displayed directly to the subject via a display which can be placed in or around food related areas or the information can be transmitted to another device. Having the information available at the time the subject is making food decisions will be a unique benefit to the user.

The device consists of:

1. A weight/bodily information device (FIG. 1) hereinafter referred to as "device" which varies from flat to flexible and varying in depth and height depending on application. The device (FIG. 1) can be placed, or manipulated to be with the use of filler panels (FIG. 6); in an area best suited for desired weight/bodily information results. The information can be transmitted to a display, another device, or memory; any, either or all, depending on user preference.

2. The display (FIG. 2) may be places in any area desired where food preparation, storage or consumption occurs. The display may be wired (FIG. 4) or wireless (FIG. 10), depending on application. The display is optional if desired use for device is transmission to another device or receiver.

3. A device power source including but not limited to battery (FIG. 3), direct wire (FIG. 4), or photovoltaic (FIG. 5).

4. The weight/bodily information device can be surrounded by filler panels (FIG. 6). The filler panels can be of various sizes, shapes or material to accommodate the desired position of the weight/bodily information device. The filler panel can also be incorporated in the weight/bodily information device (FIG. 8). The device can be made to cover the desired area by itself; therefore the use of filler panels is optional.

5. The weight/bodily information device can be covered with a device cover (FIG. 7) which can be made from any material that allows the weight/bodily information device to perform.

BACKGROUND OF THE INVENTION

The importance of a person's weight/bodily information to that person's health is generally recognized. Moreover, where the person suffers from one or more of certain types of medical conditions, weight/bodily information can have an even more important effect on the person's health.

Exercise and dieting have long been considered a necessary part of good health. The aforementioned device is used as a part of regulating a person's weight, or other personal physical conditions. It is also recommended that a person regulates the food one consumes. The problem exists that despite whatever efforts are being taken to exercise and watch what one eats, positive results are not always achieved. A large part of the problem is the over or under consumption of food. This device can assist when preparing food as a measuring tool for portion control. This tool will also display a person's weight/bodily information in places where food choices are made, weather that be in storage areas to encourage positive choices on the type of food to consume, or any other information, or consumption areas to monitor the amount of intake, or any other information, or food preparation areas to monitor portions, or any other information, or any other desired area. Having helpful information at the precise time food decisions occur, whether it is in storage, preparation or consumption area and would be helpful in controlling the unwanted behavior.

BRIEF SUMMARY OF THE INVENTION

This device is a universal weighing and bodily information device that calculates the weight and bodily information of a subject(s) in food preparation, storage and consumption areas. The information can be displayed to the user or sent to another device or location.

BRIEF DESCRIPTION OF THE DRAWING

Page 1 (FIG. 1) This shows an example of the Weight/Bodily Information Device used with refrigerator.

Page 2 (FIG. 2) This shows samples of some areas where floor model can be used. (FIG. 3) This shows display placement possibilities.

Page 3 (FIG. 4) Filler panel configuration samples. This is an example of the filler panels and several options for use. Filler panels are optional and can consist of a single panel or multiple panels. The filler panel(s) can be incorporated into the device or added to the device. The filler panels can cover all sides including top and bottom depending on the application.

Page 4 (FIG. 5) Samples of communication between device and receivers. This is an example of the communication between the device and whatever receiver the user desires. The device can communicate with a display or send a signal to an alternative device or memory. This is also an example of how communication and power may be transferred. Any combination of power sources either incorporated or tethered may be used. (FIG. 6) These are samples of communication between receivers and device. This is an example of how communication and power may be transferred.

Page 5 (FIG. 7) This drawing shows the device used in seating areas. The device can be incorporated into the seat or placed upon the seat.

Page 6 (FIG. 8) These are samples of cover panel configurations. This cover is optional and can be made of various materials depending on application.

Page 7 (FIG. 9) Shows several power options. Any combination of power sources either incorporated or tethered may be used.

Page 8 (FIG. 10) Switches drawings are an example of the switches that can be used to operate the device and/or display. The switches are optional.

DETAILED DESCRIPTION OF THE INVENTION

The proposed invention is a universal weighing and bodily information device that calculates the weight and bodily information of a subject(s) in food preparation, storage and consumption areas. The information can be transmitted to a display, another device, location, or memory; any, either, or all, depending on user preference. This device is made to be used with any food related areas and not limited to those areas mentioned. The display can be used with refrigerators, cabinets, food preparation areas, dining areas, seating areas, pantries or any other desired area. The base can be placed in desired areas with or without the use of filler panels. The base can be covered, at the user's option, with various materials that allow functionality.

The device consists of:

1. A weight/bodily information device (FIG. 1) which varies from flat to flexible and varying in depth and height depending on application. The device can be calibrated to zero and activated by either a switch or left in a constant on position. The device can be used to calculate the weight of the subject or used to calculate body information of the subject. The information can be transmitted to a display, another device, location, or memory; any, either or all, depending on user preference.

2. The display (FIG. 2) may be places in any area desired where food preparation, storage or consumption occurs. The display may be wired (FIG. 4) or wireless (FIG. 10), depending on application. The display is optional if desired use for device is transmission to another device or memory.

3. A device power source including but not limited to battery (FIG. 3), direct wire (FIG. 4), or photovoltaic (FIG. 5). The power source can be incorporated in the device or display, either or both, or tethered. Any combination of power sources can be used.

4. The weight/bodily information device can be surrounded by filler panels (FIG. 6). The filler panels can be of various sizes, shapes or material to accommodate the desired position of the weight/bodily information device. The filler panel can be several panels put together or consist of a single panel. The filler panel can also be incorporated in the weight/bodily information device (FIG. 8). The device can be made to cover the desired area by itself; therefore the use of filler panels is optional.

5. The weight/bodily information device can be covered with a device cover (FIG. 7) which can be made from any material that allows the weight/bodily information device to perform.

6. Switches can be used to turn the device and/or display on. The switches can vary in type and are not necessary. The entire unit or any part can be left in on position depending on user preference and available power.

The importance of a persons weight/bodily information to that person's health is generally recognized. Moreover, where the person suffers from one or more of certain types of medical conditions, weight/bodily information can have an even more important effect on the person's health.

Exercise and dieting have long been considered a necessary part of good health. The aforementioned device is used as a part of regulating a person's weight, or other personal physical conditions. It is also recommended that a person regulates the food one consumes. The problem exists that despite whatever efforts are being taken to exercise and watch what one eats, positive results are not always achieved. A large part of the problem is the over or under control. The base can be placed in any desired area and the subject will stand or sit on the device producing the weight and/or body information desired. The said information can either be displayed directly to the subject via a display or the information can be transmitted to another device. Having the information available at the time the subject is making food decisions will be a unique benefit to the user. This tool will also calculate a person's weight/bodily information in places where food choices are made, weather that be in storage areas to encourage positive choices on the type of food to consume, or any other information, or consumption areas to monitor the amount of intake, or any other information, or food preparation areas to monitor portions, or any other information. Having helpful information at the precise time the food decisions are made, whether it is in a storage, preparation, or consumption area and would be helpful in controlling the unwanted behavior.

Wireless electronic scales are desirable for allowing a person to weigh him or herself and view their weight/bodily information without having to look down at the scales. A need was felt for an electronic weight/bodily information apparatus that could communicate wirelessly with the display module within food preparation, storage or consumption areas, possibly be used inside or incorporated into a refrigerator, or any other desired area. The proposed device can incorporate the possibility of photovoltaic technology. The proposed device has a base that can be positioned to achieve optimum weight/bodily information results to deter, encourage, or maintain food consumption based on user needs.

The use of electronic scales is known for example, U.S. Pat. No. 4,773,492 discloses an apparatus for promoting good health that conveys weight including health-promoting messages based on departure of measured weight from ideal weight. Bodily information relating to a particular person using the scale is contained in a cartridge in electronic form. The bodily information comprises the person's ideal weight and messages related to the amount by which the person's measured departs from the ideal. The cartridge also contains provision for storing past weight measurements. When the person steps on the scale and selects his or her cartridge, weight and messages are presented on a display screen which is a portion of a television receiver. A selector switch enables the apparatus to operate in the "Scale" mode and in the "TV" mode. However, this patent does not include a universal weighing and bodily information device that calculates the weight and bodily information of a subject(s) in food preparation, storage and consumption areas. Nor can the information can be conveyed as the weight of the subject or as the addition to that weight as a measuring device. Nor can the information can be transmitted to a display, another device, location, or memory; any, either, or all, depending on user preference. Nor does it cover the use inside a refrigerator or incorporate possibility of photovoltaic technology. Nor have a base that can be positioned to achieve optimum weighing results to deter, encourage, or maintain food consumption based on user needs.

Similarly, U.S. Pat. No. 4,844,187 discloses a future weight machine that will provide an individual with personal dietary bodily information specifically tailored to the health needs of the particular individual. The apparatus includes means for determining the weight of the individual, including a weighting device. The individual will manually enter data pertaining to the age, sex, and height as well as personal dietary restrictions. The apparatus includes means for processing and analyzing the data for the individual, and means for supplying dietary bodily information pertaining to the individual. An embodiment of the invention includes means for determining weight and the pulse rate of the individual, along with an exercise during aerobic exercise. The apparatus analyzes the data and supplies statistical bodily information to the individual concerning the general physical condition of the individual. This apparatus contains means for storing the data pertaining to the individual, whereby the stored data is later recalled and used in providing bodily information of the individual. However, this patent does not include a universal weighing and bodily information device that calculates the weight and bodily information of a subject(s) in food preparation, storage and consumption areas. Nor can the information can be conveyed as the weight of the subject or as the addition to that weight as a measuring device. Nor does it cover the use inside or outside of a refrigerator, nor incorporate possibility of photovoltaic technology. Nor have a base that can be positioned to achieve optimum weighing results to deter, encourage, or maintain food consumption based on user needs.

U.S. Pat. No. 4,423,792 discloses an electronic scale apparatus and method of controlling weight that provides weight control bodily information, and a method of controlling weight which employs a scale apparatus. The apparatus comprises a scale member for measuring the weight of a person at a selected point in time. An electrical signal is generated in response to the measured weight. The apparatus further includes a memory for storing weight. This weight may include a base weight introduced previously into the memory. The apparatus includes an electronic circuit in which the generated signal is processed so that the weight of the person at the selected point in time can be compared against the base weight. This circuit also enables the calculation of a weight change based on the comparison. A display member is operatively connected to the electronic circuit for displaying the calculated weight and/or percentage of a weight change to a selected goal. The apparatus may be provided with a plurality of manually operable switches for introducing the base weight or other forms of weight related bodily information. Moreover, the apparatus may be provided with a plurality of display members for simultaneously displaying various forms of weight related bodily information. The method of the invention which may utilize the apparatus enables an individual to measure the weight over selected periods of time, receiving reinforcement for achieving a weight change, or to take corrective action based on the weight changes. However, this patent does not include a universal weighing and bodily information device that calculates the weight and bodily information of a subject(s) in food preparation, storage and consumption areas. Nor can the information can be conveyed as the weight of the subject or as the addition to that weight as a measuring device. Nor does it cover the use inside or outside of a refrigerator, nor incorporate possibility of photovoltaic technology. Nor have a base that can be positioned to achieve optimum weighing results to deter, encourage, or maintain food consumption based on user needs.

Lastly, U.S. Pat. No. 7,138,586 is a refrigerator with a weighing scale. This apparatus includes a refrigerator and a weighing scale. The refrigerator includes a chamber with top, bottom, front, rear, side surfaces, and a control board, and the weighing scale is attached to the bottom surface of the refrigerator. The weighing scale is retractable from under the bottom surface of the refrigerator. The weighing scale includes a digital scale. The digital scale includes a stepping pad and a display for showing the weight. The display of the digital scale is disposed on the control board of the refrigerator, and the display is electronically connected to the remaining portion of the digital scale. The display on the control board of the refrigerator is turned on by stepping on the stepping pad of the weighing scale, by a control switch provided on the control board, or by being pulled out from under the bottom surface of the refrigerator. This apparatus includes a refrigerator which is permanently attached to a scale and is not a universal weighing and bodily information device that calculates the weight and bodily information of a subject(s) in food preparation, storage and consumption areas. Nor can the information can be conveyed as the weight of the subject or as the addition to that weight as a measuring device. Nor can the information can be transmitted to another device, or memory; any, either, or all, depending on user preference. Nor does it cover the use inside of a refrigerator, nor incorporate possibility of photovoltaic technology. Nor have a base that can be positioned to achieve optimum weighing results to deter, encourage, or maintain food consumption based on user needs.

While the above-described devices fulfill their respective, particular objectives and requirements, the aforementioned patents do not describe a universal weighting/bodily information device with the primary function being; display the weight/bodily information of/to a person in a food preparation, storage or consumption areas. Nor do they cover the use inside a refrigerator, nor incorporate possibility of photovoltaic technology. Nor do they have a base that can be positioned to achieve optimum weight/bodily information results to deter, encourage, or maintain food consumption based on user needs.

Therefore, a need exists for a new and improved wireless electronic weight/bodily information device that can be used for electronic weight/bodily information collection that can communicate wired or wirelessly within food preparation, storage or consumption areas, and possibly be used inside, outside, or incorporated into refrigerator, cabinet, pantry, seating area or any other desired area. The proposed device can incorporate the possibility of photovoltaic technology. The device will have a base that can be positioned to achieve optimum weight/bodily information results to deter, encourage, or maintain food consumption based on user needs. In this regard, the present invention substantially fulfills this need. In this respect, the electronic weight/bodily information apparatus according to the present invention substantially departs from the conventional concepts and designs of the prior art, and in doing so provides an apparatus primarily developed for the purpose being a universal weighing and bodily information device that calculates the weight and bodily information of a subject(s) in food preparation, storage and consumption areas. The information can be transmitted to a display, another device, or memory; any, either, or all, depending on user preference. This device is made to be used with any food related areas. The display can be used with refrigerators, cabinets, food preparation areas, dining areas, seating areas, pantries or any other desired area. The base can be placed in desired areas with or without the use of filler panels. The base can be used for subjects in various positions such as sitting or standing. The base can be covered, at the user's option, with various materials that allow functionality.

PATENT CITATIONS

| Cited Patent | Filing date | Publication date | Applicant | Title |
| --- | --- | --- | --- | --- |
| U.S. Pat. No. 4,773,492 | Mar. 24, 1987 | Sep. 27, 1988 | Edward Ruzumna | Apparatus for promoting good health |
| U.S. Pat. No. 4,844,187 A | | | Thair F. Jabero | Future weight Machine |
| U.S. Pat. No. 4,423,792 | Jun. 17, 1981 | Jan. 3, 1984 | Cowan; Donald F. | Electronic apparatus and method of controlling weight |
| U.S. Pat. No. 7,138,586 | Aug. 3, 2006 | Nov. 21, 2006 | Kim; Brain S. | Refrigerator with scale |

The invention claimed is:

1. A weight and bodily information system for management of food intake by a user to be used in in food preparation, storage, and consumption areas comprising,
  a weighing system, said weighing system configured for wireless communication, said weighing system further having a first power supply component, said weighing system configured to transmit a signal reporting the users weight to a data receiving system,
  said receiving system comprised of a flat panel display, said flat-panel display configured to display weight and/or other health-relevant body information to the user while receiving weight information from said weighing system,
  said receiving system having dimensions adapted for space efficient placement in food areas including refrigerator, cupboard spaces, dining table, and countertop, said receiving system further having a second power supply component,
  said receiving system configured for wireless communication with said weighing system thereby enabling said flat-panel display to visually convey body weight information to the user.

2. The weight and bodily information system of claim 1 further comprising a filler panel, said filler panels having a plurality of recessed areas configured to receive said weighing system, thereby permitting the user to select an appropriate location to place the weighing system.

3. The weight and bodily information system of claim 2 further configured wherein said filler panel has dimensions suitable for placement on a chair.

4. The weight and bodily information system of claim 2 wherein said first and second power supply components are photovoltaic cells.

5. The weight and bodily information system of claim 2 wherein said system is configured receive data input comprised of the user's height and girth from a data input device.

6. A method for monitoring weight and bodily information for management of food intake by a user comprising,
  placing a weighing system where a user can conveniently step on the weighing system while finding items in food storage locations, said food storage locations comprising a refrigerator, a food storage cabinet, and food storage shelving, said weighing system configured such that it can be conveniently movably placed near any of said food storage locations, said weighing system having a first power supply component, said weighing system configured to wirelessly transmit a signal reporting the users weight to a receiving system,
  placing said receiving system in said refrigerator or in said food storage cabinet or on said food storage shelving, said receiving system comprised of a flat panel display device, said receiving system having dimensions adapted for space efficient placement in food areas including refrigerator, cupboard spaces, dining table, and countertop, said receiving system configured to wirelessly receive the information transmitted by said weighing system, positioning said receiving system where it can be seen by the user while the user is standing on said weighing system,
  providing power to said weighing system and said receiving system with said first and second power supply components.

7. The method for monitoring weight and bodily information of claim 6 further comprising wherein said placing step includes placing said weighing system in a recessed area of a filler panel, said filler panel having a plurality of recessed areas configured to receive sad weighing system.

8. The method for monitoring weight and bodily information of claim 7 further comprising wherein the first and second power supply components in the providing power step are photovoltaic cells.

9. The method for monitoring weight and bodily information of claim 7 further comprising wherein said weighing system or said receiving system are configured to receive data input comprised of the user's height and girth from a data input device.

* * * * *